United States Patent
Cattaneo et al.

(10) Patent No.: US 9,220,899 B2
(45) Date of Patent: Dec. 29, 2015

(54) ELECTRODE FOR MEDICAL APPLICATIONS, SYSTEM HAVING AN ELECTRODE, AND METHOD FOR PRODUCING AN ELECTRODE

(75) Inventors: Giorgio Cattaneo, Karlsruhe (DE); Alfred Stett, Reutlingen (DE); Alireza Gharabaghi, Tuebingen (DE)

(73) Assignee: Acandis GmbH & Co. KG, Pfinztal (DE)

( * ) Notice: Subject to any disclaimer, the term of this patent is extended or adjusted under 35 U.S.C. 154(b) by 43 days.

(21) Appl. No.: 13/818,663

(22) PCT Filed: Aug. 26, 2011

(86) PCT No.: PCT/EP2011/004308
§ 371 (c)(1),
(2), (4) Date: May 2, 2013

(87) PCT Pub. No.: WO2012/025246
PCT Pub. Date: Mar. 1, 2012

(65) Prior Publication Data
US 2013/0226272 A1    Aug. 29, 2013

(30) Foreign Application Priority Data
Aug. 26, 2010 (DE) .................. 10 2010 035 542

(51) Int. Cl.
*A61N 1/05* (2006.01)
*A61N 1/36* (2006.01)
(52) U.S. Cl.
CPC ............ *A61N 1/36114* (2013.01); *A61N 1/056* (2013.01); *A61N 1/0551* (2013.01); *A61N 1/0597* (2013.01)

(58) Field of Classification Search
CPC ........... A61N 1/057; A61N 2001/0585; A61N 1/0597
See application file for complete search history.

(56) References Cited

U.S. PATENT DOCUMENTS

| | | |
|---|---|---|
| 5,064,435 A | 11/1991 | Porter |
| 5,330,500 A | 7/1994 | Song |
| 5,531,779 A | 7/1996 | Dahl et al. |
| 5,645,559 A | 7/1997 | Hachtman et al. |

(Continued)

FOREIGN PATENT DOCUMENTS

| | | |
|---|---|---|
| DE | 10301600 | 7/2004 |
| DE | 69921481 | 2/2005 |

(Continued)

OTHER PUBLICATIONS

International Search Report for PCT/EP2011/004309, English translation attached to original, Both completed by the European Patent Office on Nov. 16, 2011, All together 7 Pages.

(Continued)

*Primary Examiner* — Michael Kahelin
(74) *Attorney, Agent, or Firm* — Brooks Kushman P.C.

(57) ABSTRACT

An electrode for medical applications for neuromodulation and/or nerve stimulation and/or neurological signal detection, which electrode can be compressed and expanded in order to insert same into a hollow organ of a body and is or can be coupled to a current supply. The electrode has a compressible and expandable lattice structure including lattice webs, which form cells, wherein the lattice structure is or can be coupled to the current supply and forms at least one electrically conductive region and at least one electrically insulated region.

18 Claims, 7 Drawing Sheets

(56) References Cited

U.S. PATENT DOCUMENTS

| | | | |
|---|---|---|---|
| 5,718,159 A | 2/1998 | Thompson | |
| 5,928,228 A | 7/1999 | Kordis et al. | |
| 5,954,761 A * | 9/1999 | Machek et al. | 607/126 |
| 6,099,559 A | 8/2000 | Nolting | |
| 6,169,922 B1 | 1/2001 | Alferness et al. | |
| 6,348,066 B1 | 2/2002 | Pinchuk et al. | |
| 6,445,983 B1 | 9/2002 | Dickson et al. | |
| 6,600,956 B2 | 7/2003 | Maschino et al. | |
| 6,685,736 B1 | 2/2004 | White et al. | |
| 6,709,455 B1 | 3/2004 | Chouinard | |
| 6,887,268 B2 | 5/2005 | Butaric et al. | |
| 6,934,583 B2 | 8/2005 | Weinberg et al. | |
| 7,060,089 B2 | 6/2006 | Ley et al. | |
| 7,108,716 B2 | 9/2006 | Burnside et al. | |
| 7,231,260 B2 * | 6/2007 | Wallace et al. | 607/116 |
| 7,588,597 B2 | 9/2009 | Frid | |
| 8,303,650 B2 | 11/2012 | Shokoohi | |
| 8,308,928 B2 | 11/2012 | Quandt et al. | |
| 8,801,768 B2 | 8/2014 | Karwa et al. | |
| 2003/0074039 A1 | 4/2003 | Puskas | |
| 2004/0199243 A1 | 10/2004 | Yodfat | |
| 2005/0278017 A1 | 12/2005 | Gregorich | |
| 2006/0058872 A1 | 3/2006 | Salahieh et al. | |
| 2007/0106359 A1 | 5/2007 | Schaer et al. | |
| 2007/0168019 A1 | 7/2007 | Amplatz et al. | |
| 2007/0198075 A1 | 8/2007 | Levy | |
| 2008/0262593 A1 | 10/2008 | Ryan et al. | |
| 2008/0262594 A1 | 10/2008 | Morris | |
| 2009/0024195 A1 | 1/2009 | Rezai et al. | |
| 2009/0088833 A1 | 4/2009 | Soetermans | |
| 2009/0127226 A1 | 5/2009 | Quandt et al. | |
| 2009/0248133 A1 | 10/2009 | Bloom et al. | |
| 2009/0319029 A1 | 12/2009 | Evans et al. | |
| 2010/0049310 A1 | 2/2010 | Quandt et al. | |
| 2011/0046718 A1 | 2/2011 | Cattaneo et al. | |
| 2011/0093002 A1 | 4/2011 | Rucker et al. | |
| 2012/0277788 A1 | 11/2012 | Cattaneo | |
| 2012/0323309 A1 | 12/2012 | Cattaneo | |
| 2014/0058436 A1 | 2/2014 | Rosenbluth et al. | |

FOREIGN PATENT DOCUMENTS

| | | |
|---|---|---|
| DE | 102005018731 | 10/2006 |
| DE | 102006007231 | 8/2007 |
| DE | 60128588 | 2/2008 |
| DE | 102006039840 | 3/2008 |
| DE | 102007061931 | 6/2009 |
| DE | 102008010507 | 8/2009 |
| DE | 102009056450 | 6/2011 |
| DE | 102009060228 | 6/2011 |
| DE | 102009060280 | 6/2011 |
| EP | 1304135 | 4/2003 |
| EP | 1374799 | 1/2004 |
| EP | 1645246 | 4/2006 |
| WO | 2005110528 | 11/2005 |
| WO | 2007039587 | 4/2007 |
| WO | 2007105060 | 9/2007 |
| WO | 2008009434 | 1/2008 |
| WO | 2008094789 | 8/2008 |
| WO | 2011049823 | 4/2011 |

OTHER PUBLICATIONS

Non-Final Office Action for U.S. Appl. No. 13/818,664, Dated Dec. 17, 2014, 22 Pages.

Non-final Office Action for U.S. Appl. No. 13/818662 dated Oct. 7, 2015.

* cited by examiner

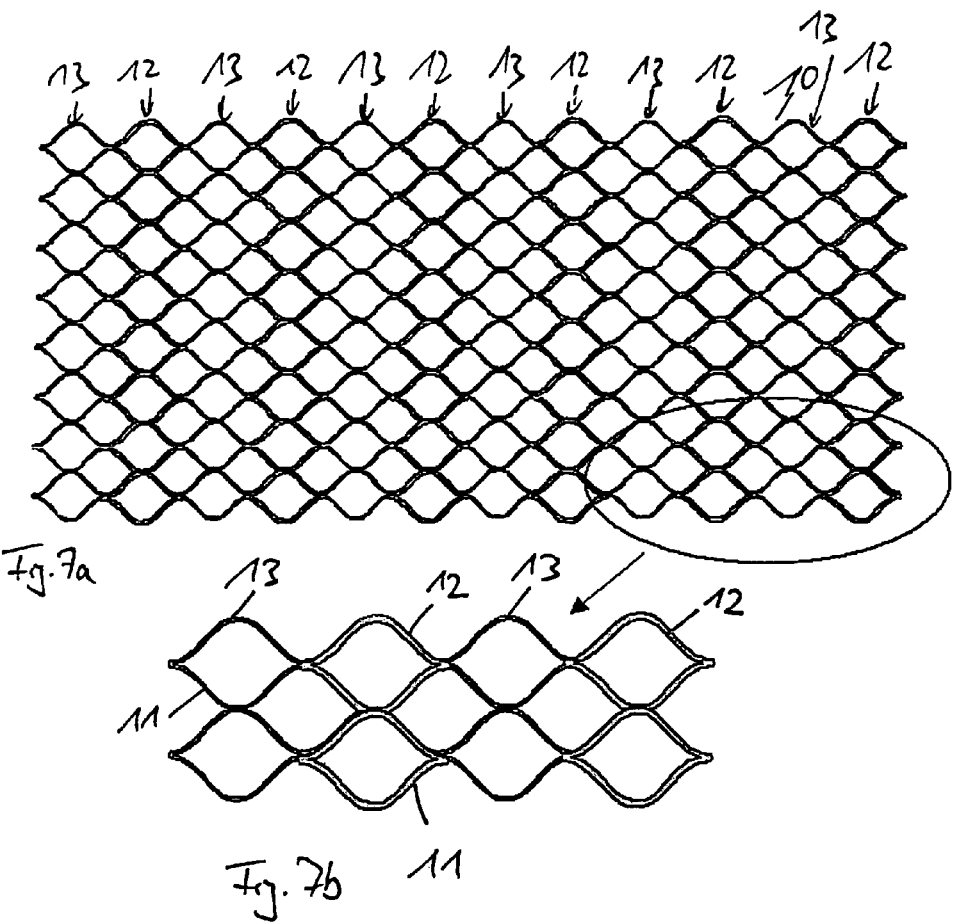
Fig. 7a
Fig. 7b
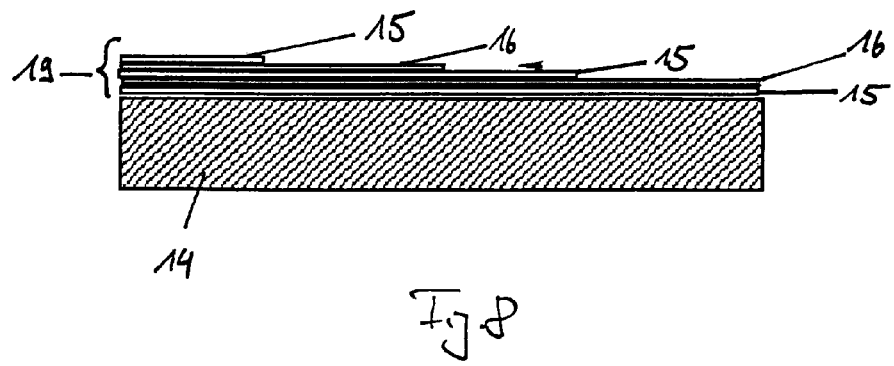
Fig. 8

ELECTRODE FOR MEDICAL APPLICATIONS, SYSTEM HAVING AN ELECTRODE, AND METHOD FOR PRODUCING AN ELECTRODE

CROSS-REFERENCE TO RELATED APPLICATION

This application is the U.S. national phase of PCT Appln. No. PCT/EP2011/004308 filed on Aug. 26, 2011, which claims priority to German Patent Application No. 10 2010 035 542.9 filed on Aug. 26, 2010, the disclosures of which are incorporated in their entirety by reference herein.

The invention relates to an electrode for medical applications for neuromodulation and/or nerve stimulation and/or neurological signal acquisition, which is compressible and expandable for introduction into a hollow organ of a body and is coupled or couplable to an electrical supply. An electrode of this type is known, for example, from U.S. Pat. No. 5,531,779.

The known electrode is used for the treatment of heart defects, and is configured for the transmission of relatively strong currents which are necessary for such treatments. The electrode is formed as an endovascular stent, which is produced from a steel alloy and is conductive overall. The stent as a whole therefore forms the probe, which is compressible and expandable for introduction into the body. In order to generate an electric field, the stent electrode is combined with a further electrode, for example configured in the form of a second stent electrode, which is implanted at a distance from the first stent electrode and is polarized differently.

The known stent electrode is constructed from individual wires, which extend essentially parallel in the expanded state and are formed in the manner of a basket. Other stent structures based on wires, for example woven or meshed stents, are disclosed as suitable. The known system allows only imprecise and poorly modulatable stimulation of larger body regions.

A similar electrode, which is likewise used for heart treatment, is known from US 2003/74039 A1. The electrode is used with a further additional electrode, in order to generate an electric field.

Electrodes are furthermore known in which the electrode poles are integrated into the same implant, so that the second separate electrode can be obviated. For example, U.S. Pat. No. 6,445,983 B1 discloses a stent electrode, on the outer surface of which a first and a second electrode, which are driven by a radio signal, are fastened. Another example of an implantable electrode, in which the two poles are arranged in the same implant, is known from WO 2008/09434 A1, which discloses a spiral shaped wire on which different electrode regions, or poles, are provided. The various electrode regions can be driven independently of one another, so that the electric field generatable with the electrode is modulatable. A similar electrode is known from WO 2008/094789 A1, which has a stent structure for anchoring the electrode wire. This stent structure is connected to the electrode wire so that the electrode wire is pressed onto the vessel wall by expansion of the carrier stent. The stent is in this case used exclusively as a mechanical support. Another electrode consisting of a wire comprising different polarizable electrode regions is known from EP 1 304 135 A2.

Production of the aforementioned electrodes is complicated, since either elaborate joining techniques are required therefor or the electrical supply of the individual electrode regions is difficult to produce. Furthermore, the electrodes connected to the support structure are comparatively large, so that on the one hand the number of electrodes is limited and, on the other hand, precise modulation of the electric fields is only limitedly possible. Some of the known systems require lines which are connected to the electrode and must correspondingly be insulated, since otherwise contact with the carrying structure of the electrode would lead to a short circuit. The insulated lines increase the complexity and unwieldiness of the systems and make delivery more difficult, particularly into small vessels.

It is an object of the invention to provide an electrode for medical applications, which has improved modulation properties. The invention is furthermore intended to provide a system having such an electrode and a method for producing such an electrode.

According to the invention, the object is achieved in relation to the electrode by the subject-matter of claim 1. In relation to the system, the object is achieved by the subject-matter of claim 19, and in relation to the method for producing the electrode it is achieved by the subject-matter of claim 21.

The invention is based on the concept of providing an electrode for medical applications for neuromodulation and/or nerve stimulation and/or neurological signal acquisition, which is compressible and expandable for introduction into a hollow organ of a body and is coupled or couplable to an electrical supply. The electrode comprises a compressible and expandable lattice structure comprising lattice webs which form cells, the lattice structure or at least one section of the lattice structure being coupled or couplable to the electrical supply and forming at least one electrically conductive region and at least one electrically insulated region.

The electrode according to the invention differs from the known systems, in particular from the system according to U.S. Pat. No. 5,531,779, in that the lattice structure is formed from lattice webs which form cells. It is thus not a lattice structure based on individual wires, as in the case of a mesh, but a lattice structure based on lattice webs. The lattice webs are preferably arranged flush with one another in a single wall plane. Furthermore, in contrast to individual wires, the lattice webs are connected firmly to one another at intersection points, in particular connected with a material fit, and therefore also lie in the same plane in the region of the intersection points. A lattice structure consisting of lattice webs is, for example, produced by etching or cutting from a solid material, the openings which form the cells being cut out from the solid material so that the lattice webs, which delimit the cells, remain. An alternative to this is production of the lattice structure by deposition methods, for example PVD methods in which the material of the lattice webs is deposited on a substrate. In this case as well, a lattice structure comprising lattice webs is obtained, which differs from the known meshed structures in terms of shape and structure, as wires or filaments are not provided in this case. The lattice structure may be produced fully by the PVD method and may be self-supporting. As an alternative, a lattice structure produced in another way from solid material may be used as a carrier structure, which is coated by a PVD method. It is possible to produce stent-like lattice structures. These may, in a manner known per se, be formed as small tubes or rolled starting from a planar shape. A method for producing a planar lattice structure is disclosed, for example, in DE 10 2006 039 840 A1, which is in the name of the Applicant. The lattice structure may be planar in the implanted state or have a different geometrical shape.

Another difference from the known systems is that the lattice structure forms at least one electrically conductive region and at least one electrically insulated region. The at least one electrically conductive region has the function of at least one electrode pole, or the electrically conductive region have the function of two or more than two electrode poles, which are formed by the lattice structure itself, i.e. they are integrated into the lattice structure or form a part of the lattice structure. In other words, elements of the lattice structure, in particular the lattice webs and/or surface elements, which are respectively applied on individual lattice webs belong to the lattice structure and together therewith carry out the crimp movement or deformation when crimping form the poles of the electrode. In contrast thereto, the poles of the known electrodes are applied onto an outer surface of the lattice structure, which therefore undertakes only a mechanical carrying function.

An electrically conductive region and an insulated region are respectively intended to mean a delimited region of the lattice structure (wall region), extending in the plane of the lattice structure, or in the wall plane. In the case of a stent-like electrode, the wall plane corresponds to the outer lateral surface of the electrode. The electrically conductive region is delimited by at least one electrically insulated region, which is arranged in the same plane as the electrically conductive region and delimits the electrically conductive region at least in sections. The electrically conductive region and the electrically insulated region are arranged in the same plane of the lattice structure. The electrically conductive region and the electrically insulated region are integrated in a surface of the lattice structure, particularly in an outer surface and/or in an inner surface of the lattice structure. The outer surface faces toward the tissue in the implanted state. In the case of rolled electrodes, the allocation of the electrically conductive and electrically insulated regions to the outer surface or to the inner surface can be determined simply by the rolling direction. In the case of a stent-like lattice structure, the electrically conductive region extends in the longitudinal direction and/or in the circumferential direction of the lattice structure, or in the outer lateral surface. In general, the electrically conductive region and the electrically insulated region respectively form a subregion of the lattice structure, these being arranged next to one another. The same applies for a plurality of electrically conductive and insulated regions.

The electrode according to the invention has various advantages: since the poles, or the at least one pole, of the electrode are a component of the lattice structure, the joining techniques sometimes used in the prior art are not necessary. By the formation of the at least one electrically conductive region and at least one electrically insulated region, in particular by the formation of a plurality of electrically conductive and insulated regions, in the form of the lattice structure, the precision of the nerve stimulation and of the acquisition of signals on the basis of nerve activities is improved. This is because very fine structures electrically insulated from one another, and therefore a large number of electrode regions which can be stimulated independently of one another, can be provided with the invention. A high resolution can therefore be achieved both for the stimulation or modulation of nerves, and for the signal acquisition. In the scope of the invention, it is possible to insulate individual lattice webs or even parts of individual lattice webs electrically from one another, so that a correspondingly finely subdivided electrode structure is formed. As a result of the use of the lattice structure as an electrode region, flexible adaptation of the electrode regions to different application cases is achieved, since larger or smaller electrode regions can be formed in almost any desired way depending on the application case. The electrode may have a single electrically conductive region and a single electrically insulated region. In this case, a further electrode is necessary for the mating pole. Integrating the single pole of the electrode according to the invention into the lattice structure has the advantage that the system is compact and robust, since the risk of detaching an electrode is virtually excluded, in contrast to known electrodes having externally applied poles.

In order to integrate both poles into the lattice structure, at least two electrically conductive regions are provided, which may be polarized differently or in the same way.

The lattice structure has a double function, since it fulfills both a mechanical function as a carrier or support function, and an electrical function as an electrode. The space requirement of the electrode according to the invention is therefore improved in relation to known electrodes, since space is saved by the formation of the lattice structure itself as an electrode, compared with known electrodes in which the electrode poles are applied separately on the implant. This in turn makes it possible to treat smaller vessels, particularly in the cerebral region, by electrodes.

The electrode according to the invention is also suitable for neurological applications, particularly in the field of sensor technology.

Preferred embodiments of the invention are specified in the dependent claims. Thus, at least one section of the lattice structure and the entire lattice structure may be constructed in layered fashion. Owing to the layered design, the lattice structure can be subdivided particularly well into electrically conductive and electrically insulated regions. This contributes to the space requirement of the electrode being smaller in comparison with known electrodes. In this case, the electrically conductive region and/or the electrically insulated region, in particular the electrically conductive region, may respectively be constructed in layered fashion.

The electrically conductive regions and electrically insulated regions may be arranged at different positions along the lattice structure, the electrically conductive regions being separated from one another by the electrically insulated regions. As an alternative or in addition, the conductive region may be arranged on an outer surface and/or on an inner surface of the lattice structure. It is therefore possible to arrange, or position, the poles of the lattice structure distributed in different directions along the lattice structure, that is to say in directions along the wall of the electrode. The electrically conductive region may additionally be provided in the outer surface and/or in the inner surface of the lattice structure, and therefore be arranged in the thickness direction of the wall. This means that the poles of the electrode may be integrated in different directions along the lattice structure into the outer surface and/or into the inner surface of the lattice structure.

The lattice structure, constructed in a layered fashion, may have a carrier layer, at least one insulator layer and at least one electrically conductive layer. This basic configuration of the lattice structure allows straightforward formation and separation of the electrically conductive and electrically insulated regions. The electrically conductive region comprises the electrically conductive layer, which can be omitted in the electrically insulated region. Owing to the functional separation, the mechanical properties of the lattice structure can be optimized separately when forming the carrier layer from the electrical properties of the lattice structure when forming the insulator layer and the electrically conductive layer. It is also possible to form the entire carrier layer from an insulating material, so that the carrier layer simultaneously forms the insulator layer. It is likewise possible to form the carrier layer from an electrically conductive material, in such a way that the carrier layer simultaneously forms the electrically conductive layer and is provided with an insulator layer. This means that at least two layers, an insulator layer and a conductive layer, are sufficient at least in the electrically conductive region. The electrically insulated region may consist only of the insulator layer (single layer). This concept may be extended, so that the electrically conductive region has more than two layers and the electrically insulated region has more than one layer. The further layers may comprise mechanically supporting layers and further insulator layers and conductive layers.

In order to form the electrically conductive region, the insulator layer may be arranged between the carrier layer and the electrically conductive layer. For the carrier layer, it is therefore possible to use conventional materials known per se in the production of lattice structures, for example metallic materials such as shape memory materials, such as Nitinol, or steel or bioabsorbable materials, for example magnesium, magnesium alloys or other alloys. Owing to the insulation of the electrically conductive layer from the carrier layer, a voltage can be applied to the electrically conductive layer without current flowing through other regions of the lattice structure, for example the carrier layer or other lattice regions, which are mechanically connected to the carrier layer of the electrically conductive region. In the electrically insulated region, the insulator layer may form the outer layer of the lattice structure.

In another embodiment, the lattice structure has at least one line unit comprising at least two insulator layers, an electrically conductive layer being arranged between a first and a second insulator layer. By virtue of the line unit insulated on both sides, different electrically conductive regions can be supplied with electricity independently of the arrangement of the respective regions.

The first insulator layer may form the outer layer in the electrically insulated region and, in the electrically conductive region, be connected to a further electrically conductive layer which is arranged on the first insulator layer. The electrically conductive layer in this case forms the outer layer in the electrically conductive region. By the alternating arrangement of the electrically conductive layer and the insulator layer, delimitation of the electrically insulated and electrically conductive regions can be achieved in a straightforward way.

The lattice webs may have, in the electrically conductive region, an electrically conductive widening which extends in the longitudinal direction of the lattice webs in such a way that the region of the lattice webs coming into contact with the hollow organ is wider than the region of the lattice webs at a distance from the hollow organ. The area of contact of the electrically conductive region with the tissue is thereby increased, so that a gentle treatment is made possible.

In another preferred embodiment, at least one lattice web, in particular a plurality of lattice webs, are respectively connected to at least one electrically conductive cover, the longitudinal direction of which differs from the longitudinal direction of the lattice web in such a way that the cover extends into at least one adjacent cell and at least partially covers the latter. Owing to the cover, the geometrical shape of the respective poles, or electrically conductive regions, can be varied. Furthermore, in this embodiment as well the area of contact with the hollow organ is thereby increased, so that a gentle treatment is made possible.

The size and/or geometry of the covers may be at least partially equal or different. The geometry of the cover may be selected in virtually any desired way. In addition or as an alternative, the number of covers may vary on the circumference of the lattice structure and/or in the longitudinal direction of the lattice structure. The modulation properties of the electrode can therefore be influenced. The web widenings and the covers may be combined with one another. In this case, it is possible to configure the mixed forms consisting of web widenings and covers in such a way that the web widenings do not extend continuously parallel to the webs, but project in departure from the longitudinal direction of the web.

A plurality of covers may be connected to one another by the electrically conductive layer, in particular by a line unit. In this way, a plurality of covers can be driven together, so that the modulation capacity of the electrode is further improved.

Preferably, different electrically conductive regions can be interconnected with one another, in particular variably interconnected with one another, for the modulation of electric fields. The shape, arrangement and strength of the electric fields can therefore be varied. Preferably, the electrically conductive regions, or the at least one electrically conductive region, are adapted for the generation of electric fields and/or for signal acquisition on the basis of nerve activities. The electrode can therefore be used for the stimulation of nerves and/or for the detection of nerve activities. In this case, both the stimulation function and the detection function, or correspondingly adapted electrodes, are disclosed per se and in combination with one another.

The electrically conductive regions may, in principle, be distributed in virtually any desired way in the lattice structure. Preferably, a plurality of electrically conductive region are arranged mutually parallel in a direction along the lattice structure and respectively separated from one another by an electrically insulated region. The electrically conductive regions may also be arranged in series in a direction along the lattice structure and respectively be separated by an electrically insulated region.

The driving of the different electrically conductive regions may take place by carrying it out with the electrical supply through electrically conductive layers along various lattice webs electrically insulated from one another. In addition or as an alternative, the driving may be carried out in that different electrically conductive regions are coupled or couplable by a plurality of line units in at least one lattice web. The routing of the electrical supply is flexible, and therefore gives the greatest possible freedom in the arrangement of the electrical regions in the lattice structure. By using the lattice webs as electrical conductors, in comparison with the prior art a very compact structure of the electrode is achieved, which may be correspondingly miniaturized and may be implanted in correspondingly small cavities, particularly in small vessels, without being restricted thereto.

A system having an electrode as described above, an electrical supply, a pulse generator and control electronics, which are coupled or couplable to the electrode, is furthermore disclosed and claimed. This means the invention relates both to the electrode per se, i.e. independently of the overall system, and to the overall system comprising such an electrode.

The system may comprise at least one further electrode for medical applications, which interacts with the electrode according to the invention, or an electrode according to one of the embodiments of the invention as mentioned above.

The application possibilities of the electrode are thereby extended, the arrangement of the electrical regions integrated into the lattice structure also being advantageous in connection with a separate electrode. The further electrode may for example be an extracorporeal electrode, a further implantable electrode or the catheter tip of an associated delivery system.

The method for producing the electrode is based on the lattice structure being produced at least partially by physical vapor deposition, various materials being deposited layer-wise on a substrate and structured in such a way that a self-supporting lattice structure or a coated lattice-like carrier structure comprising at least one electrically conductive region and at least one electrically insulated region is formed. The use of PVD methods, in particular sputtering methods, for producing the electrode makes it possible to form lattice webs with various layers of different materials. Insulator layers and electrically conductive layers can therefore be applied and modified along the lattice structure in a controlled way, so that it is possible to form electrical regions and insulated regions which are arranged in virtually any desired way. The method according to the invention thus permits very flexible production of the electrode, in which case the different regions can be arranged according to the requirement of the electrode and formed with a view to the geometrical shape of the regions. Other production methods may be envisioned, in which the insulator layers or electrically conductive layers are applied onto the carrier layer in another way, for example by photolithography methods.

The invention will be further explained with more details below with the aid of exemplary embodiments with reference to the appended schematic drawings, in which:

FIG. 7a shows a plan view of an electrode according to another exemplary embodiment according to the invention;

FIG. 7b shows a detail of the lattice structure of the electrode according to FIG. 7a;

FIG. 8 shows a lateral view of the lattice structure according to FIG. 7b with a plurality of electrically conductive layers;

Figure 1:
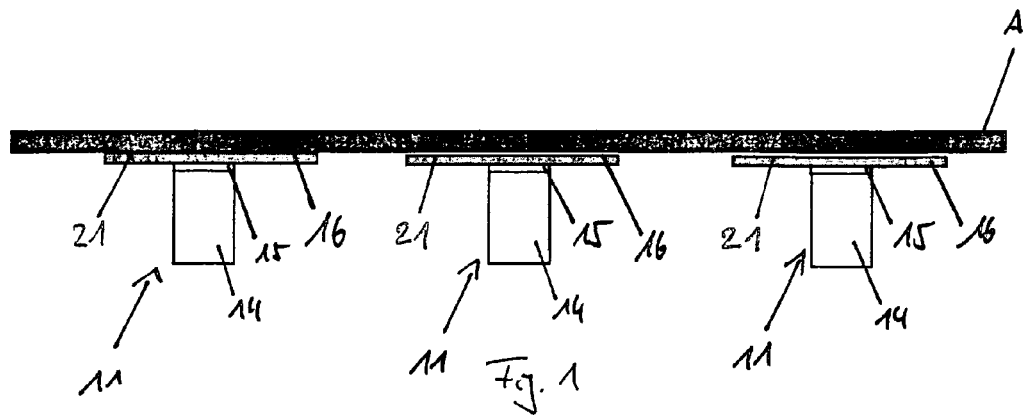
FIG. 1 shows a longitudinal section through the lattice structure of an electrode according to an exemplary embodiment according to the invention in the implanted state.
Figure 2:
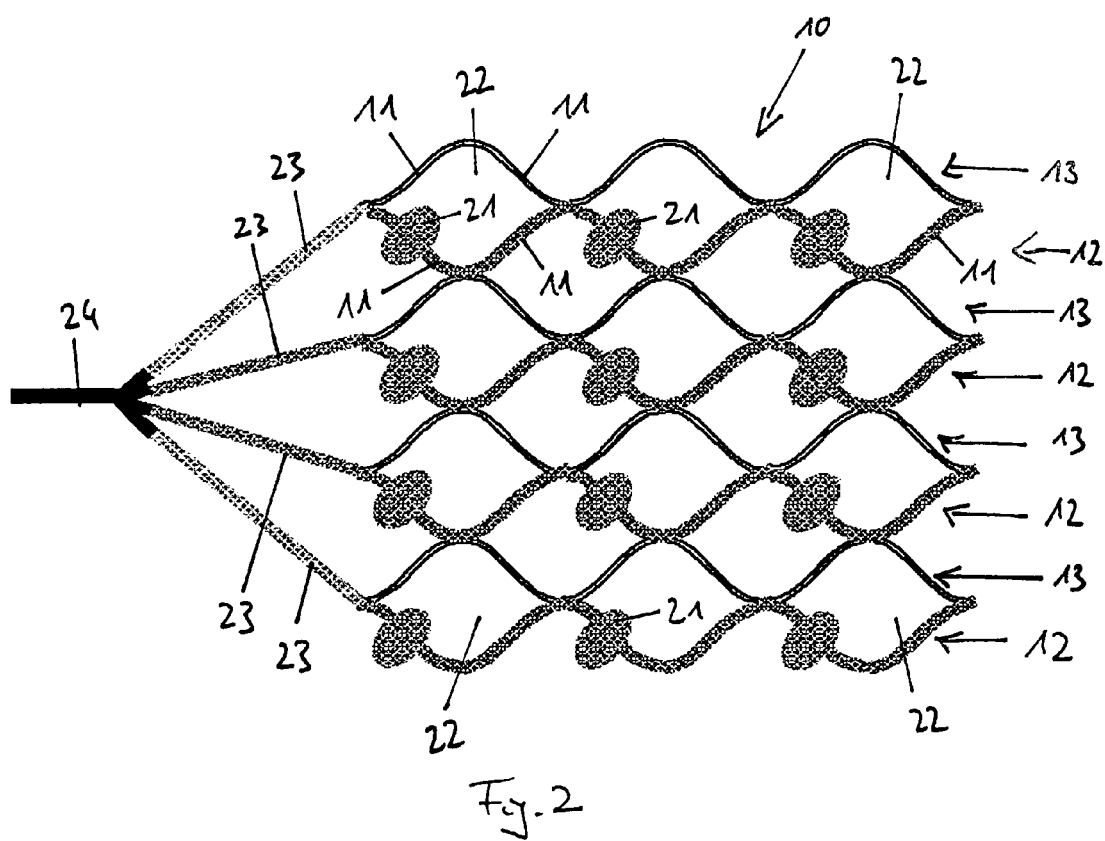
FIG. 2 shows a plan view of the electrode according to FIG. 1.

FIGS. 1 and 2 represent an example of an electrode according to the invention, which has various different electrically conductive and electrically insulated regions 12, 13 integrated into the lattice structure 10. The implantable electrode for medical applications, in particular but not exclusively for endovascular medical applications, may be arranged temporarily or permanently in a hollow organ of a body or is adapted therefor. The electrode is suitable for use in large and small vessels, for example coronary vessels or intracranial vessels, and in both arteries and veins, for example the carotid artery or the jugular vein. To this end, the electrode has a lattice structure 10, which is formed from lattice webs 11. In a manner known per se, the lattice webs 11 form cells 22. To this end, the lattice webs 11 are locally connected to one another, or have connectors which connect the webs in order to form the cells 22. The lattice structure 10 may have an open-cell or closed-cell structure (open-cell design, closed-cell design). Such structures are known to the person skilled in the art. The lattice structure 10 based on lattice webs 11 differs from wire meshes which likewise form lattice structures, not on the basis of lattice webs but rather on the basis of filaments or wires. Lattice meshes have different mechanical properties to lattice structures consisting of lattice webs 11 and differ particularly in terms of production. The advantages achievable according to the invention in relation to the various electrically conductive and electrically insulated regions 12, 13 integrated into the lattice structure are not possible in the case of meshes, or possible only with relatively great difficulties. Conversely, the methods used for the production of lattice structures 10 based on lattice webs 11 are suitable for forming regions with different electrical properties in the lattice structure 10. In this case, deposition methods are primarily suitable, with the aid of which different types of layers that have different electrical properties can be constructed in a comparatively straightforward way. The invention is not restricted to production by such PVD methods, but also comprises other methods with which lattice structures having different electrical regions which are constructed layer-wise can be produced. For example, bonding techniques with which various layers can be applied to one another may be envisioned.

The shape of the lattice structure 10 corresponds to the shape of a stent. The lattice structure 10 is rotationally symmetrical, in particular hollow-cylindrical. The exemplary embodiment according to FIGS. 1, 2 is thus a stent electrode, i.e. an electrode having a tubular lattice structure. The lattice structure may also be produced in planar form and then rolled, in particular rolled and laterally sealed (welded) or may be laterally open. The invention also comprises lattice structures with a different shape, for example filters or flow diverters. In general, the lattice structure may have any desired compressible and expandable shape which is suitable for being introduced into a hollow organ by a delivery system.

Mechanical properties of the electrode, including the crimpability, correspond to the mechanical properties of stents known per se or other known endovascular implants.

The electrode according to FIG. 2 is a bipolar electrode, in which at least two different electrode poles are integrated into the lattice structure. The poles are electrically insulated from one another and correspond to the various electrically conductive regions 12 represented in FIG. 2. It is therefore possible to generate electric fields with the electrode, without a further electrode as a mating pole being required therefor.

The poles may also have the same polarity applied to them and be used together with an additional electrode, which forms the mating pole for the electrically conductive regions 12 arranged on the electrode according to FIG. 2. The mating electrode may be provided extracorporeally and act transcutaneously. It is also possible to provide a further implantable electrode if appropriate also having a plurality of electrically conductive regions 12 or electrode poles corresponding to the electrode according to FIG. 2. It is furthermore possible to form part of a delivery system (not shown), for example a catheter tip or a guide wire, as a mating electrode.

The electrode is coupled to an electrical supply, or is couplable to an electrical supply. To this end, the electrode, or the lattice structure 10, may be connected by a line to an electrical supply (not shown). The electrical supply of the electrode may be formed as a module together with a pulse generator and control electronics.

For connection of the electrode to the electrical supply, or the module, FIG. 2 represents a central supply line 24 which combines a plurality of individual supply lines 23, or electrical cables. The supply lines 23 are insulated, both inside and outside the central supply line 24, so that different voltages can be applied to them independently of one another. The central supply line 24 may fulfill a mechanical function and, for example, be formed as an actuation means for the delivery or retraction of the electrode. The individual supply lines 23 are connected to the various electrically conductive regions 12 of the lattice structure. In the exemplary embodiment according to FIG. 2, four supply lines 23 are provided. A different number is possible, corresponding to the number of electrically conductive regions of the electrode which are to be driven.

The module may be fitted in a likewise implantable housing.

On the other hand, it is possible for the connection between the electrical feed and the electrode to be carried out wirelessly, for example by induction of an electric current in the lattice structure 10 by means of a transcutaneous energy transfer system (TET system). To this end, the electrode has a means for coupling to an electrical feed, or has an electrical transmission means, in particular for inductive electrical transmission, which is connected to the lattice structure, in particular to the at least one electrically conductive region 12. In this case, the electrode comprises a receiver, in particular a reception coil, which is electrically coupled to the electrically conductive regions 12 of the lattice structure 10 and can be excited by an extracorporeal transmitter or an extracorporeal transmission coil, so that an electric voltage is induced in the reception coil. In addition to the reception coil, it is possible to provide a pulse generator and control electronics which are connected to the lattice structure 10. The pulse generator and the control electronics may also be provided extracorporeally and communicate by radio with the reception coil, or a suitable receiver. It is furthermore possible to integrate a rechargeable battery into the electrode, which can be recharged by the reception coil by a charging device. Such systems for transcutaneous energy transmission (TET systems) are known per se and may be used together with the invention. As an alternative, a battery which is lifelong functional, or at least configured for the duration of the treatment, may be used. Both the electrode per se, with the means for coupling to an electrical feed, and the system described above, having such an electrode, are disclosed.

For short-term treatments, the electrode may be connected to cables.

The stent electrode therefore differs from exclusively mechanically acting stents inter alia in that the electrode is coupled to an electrical supply, or at least comprises means by which the electrical supply of the electrically conductive regions 12 can be achieved. Furthermore, in the case of exclusively mechanically acting stents the lattice structure is not subdivided into electrically conductive and electrically insulated regions, as in the case of the invention.

In the scope of the invention, both the electrode per se and the system comprising an electrode are claimed, as well as electrical devices, for example an electrical supply, pulse generator and control electronics.

As represented in FIG. 2, the various poles of the electrode are integrated into the lattice structure. To this end, the lattice webs 11 of the electrode 10 are formed in such a way that a voltage can locally be applied to them, or different voltages can be locally applied to them. The current-carrying lattice webs 11 are electrically insulated from noncurrent-carrying lattice webs 11. This will be explained by way of example elsewhere with reference to the layer-wise structure of the lattice webs 11. The lattice webs 11 locally form the poles of the electrode, or the electrically conductive regions 12. A further function of the lattice webs 11 is to supply discrete, or separately arranged electrically conductive regions 12 with electricity.

The various electrically conductive regions 12 may, as represented in FIG. 2, be arranged in different directions along the lattice structure 10. For example, it is possible to arrange the electrically conductive regions in the longitudinal direction of the stent-like lattice structure. The electrically conductive regions in this case essentially extend mutually parallel and follow the profile of the lattice webs 11. This leads to a more meandering shape of the electrically conductive regions 12. The electrically conductive regions 12 are separated from one another by electrically insulated regions 13, which likewise extend parallel in the longitudinal direction of the stent-like lattice structure. In the present exemplary embodiment, four electrically conductive regions 12 are provided. As can be seen in FIG. 2 each electrical region 12 is assigned its own supply line 23 which is electrically connected to the respective electrical region 12. In order to avoid short circuits and for independent voltage supply, the supply lines 23 are insulated. The supply lines 23 may be formed with multiple layers, in a manner corresponding to the structure of the lattice structure 10. The supply lines 23 are clad with insulation.

The number and arrangement of the electrically conductive regions may be extended in virtually any desired way. In the extreme case, the electrode has a single electrically conductive region and a single electrically insulated region. In this case, a further electrode is required in order to generate the electric field. Preferably, at least two electrically conductive regions are integrated into the lattice structure 10, so that the lattice structure 10 forms both poles of the electrode. The electrically conductive regions 12 are electrically separated from one another by electrically insulated regions 13.

The electrically insulated regions 13 are arranged in the circumferential direction, respectively between two electrically conductive regions 12, and they likewise extend mutually parallel. In the exemplary embodiment according to FIG. 2 the electrically conductive and electrically insulated regions 12, 13 are thus arranged at different positions along the lattice structure. In this case, the arrangement along the lattice structure means that the different regions 12, 13—in the case of a stent-like electrode—extend in the longitudinal direction and/or in the circumferential direction of the electrode, or are arranged in these directions. The electrically conductive regions 12 may also be arranged in the thickness direction, i.e. in the radial direction of the lattice structure 10, so that an electrically conductive region 12 forms either the outer surface or an inner surface of the lattice structure 10. A combination, with inner and outer surfaces respectively being formed by electrically conductive regions, which are separated from one another by an insulator layer, is likewise possible. A combination of the different regions 12, 13 arranged along the lattice structure 10 and of the electrically conductive and electrically insulated regions 12, 13 arranged in the radial direction is likewise possible. In the exemplary embodiment according to FIG. 2, the electrically conductive and electrically insulated regions 12, 13 are arranged only along the lattice structure, the electrically conductive regions 12 forming the outer surface of the lattice structure, come into contact with the hollow organ of the vessel wall in the implanted state. The lumen, or the inner surface, of the lattice structure 10 according to FIG. 2 is continuously insulated from the locally electrically active outer surface.

The basic configuration of the lattice structure 10 according to FIG. 2 is represented in FIG. 1. It can be seen there in that the individual lattice webs are constructed layer-wise. This applies at least for the electrically conductive regions 12.

The lattice structure 10 of the electrode may have a plurality of material layers with different properties, or functions. The layers may consist of different materials or the same materials, i.e. the same chemical compositions, and differ in their structural properties. For all exemplary embodiments and embodiments, it applies that at least one layer at least locally has the structural properties, achievable by the PVD method, which are disclosed in this application. It is possible for all layers to have the desired structural properties. The structural properties are set by the PVD method, in particular by sputtering. For example, the conductive region, in particular the outer layer, may have the desired structural properties and is produced by the PVD method. The carrier structure is produced in a conventional way, for example by laser cutting. This has the advantage that the outer layer having the improved material properties comes into contact with the tissue. When the entire lattice structure in the radial direction, i.e. all layers are arranged above one another, is produced by the PVD method, both mechanical and electrical properties of the electrode are improved. The layer thickness with the sputtered material is at least 2%, in particular at least 5%, in particular at least 10%, in particular at least 15%, in particular at least 20%, in particular at least 25%, in particular at least 30%, in particular at least 35%, in particular at least 40%, in particular at least 45%, in particular at least 50%, in particular at least 55%, in particular at least 60%, in particular at least 65%, in particular at least 70%, in particular at least 75%, in particular at least 80%, in particular at least 85%, in particular at least 90%, in particular at least 95%, in particular 100%, of the wall thickness of the lattice structure.

The lattice webs 11 respectively have a carrier layer 14, which is respectively arranged inward in relation to the curved shape of the lattice structure 10, and therefore delimits the lumen of the electrode. An insulator layer 15 is applied radially further outward on the carrier layer 14, and a conductive layer 16 is applied on the insulator layer 15. The insulator layer 15 separates the carrier layer 14 from the electrically conductive layer 16 so that short circuits between the different electrode poles or electrically conductive regions 12 are avoided. The insulator layer 15 need not necessarily form absolute electrical insulation in the sense that the flow of current between the electrically conductive layer 16 and the carrier layer 14 is completely prevented. For correct functioning of the electrode, it may be sufficient to permit a leakage current.

For the separation of the conductive and insulated regions 12, 13, two possibilities may be envisioned: only the electrically conductive layer 16 carries current, but not the carrier layer 14, for example by only the electrically conductive layer 16 of the respective conductive regions 12 being connected to a supply line 23. It is then sufficient to insulate the conductive layer 16 from the carrier layer 14 in the conductive regions 12. In the insulated regions 13, the carrier layer 14 may form the outer surface, i.e. without an insulator layer 15. The insulator layer 15 may naturally also be provided in the insulated regions 13. In the electrode according to FIGS. 1, 2, 3, 4, the lattice webs in the electrically insulated region 13 are constructed layer-wise, the radially outwardly arranged layer forms the insulator layer 15. The carrier layer 14 may be formed from an electrically conductive material, for example Nitinol. Owing to the insulation of the carrier layer 14 in the conductive region 12, short circuits do not take place. In this preferred exemplary embodiment, the individual poles can be driven independently of one another.

As an alternative, electricity may be applied fully to the carrier layer 14, i.e. in the region of the entire lattice structure 10, the carrier layer being locally insulated, i.e. carrying the insulator layer 15 (insulated regions 13) and locally uninsulated. In these regions, the carrier layer 14 forms the outer surface of the lattice structure (conductive regions 12). In this case, only the same voltage can be applied to all the poles of the electrode.

As can be seen in FIG. 1, the thickness of the carrier layer 14 is greater than the layer thickness of the insulation layer 15, or of the electrically conductive layer 16. The thickness of the carrier layer is dictated by the mechanical properties of the electrode, or of the lattice structure 10 of the electrode, for example by the radial force which the electrode is intended to exert on the vessel wall in the expanded state. The thickness of the carrier layer 14 may be determined by the person skilled in the art as necessary. The thickness of the other layers 15, 16 is dictated by both the mechanical and electrical requirements, which are placed on the electrode.

In the simplest case, the lattice webs 11 in the electrically conductive region 12 form the respective pole of the electrode. In this case, the contour of the electrically conductive layer 16 corresponds to the web contour.

In order to achieve a gentle treatment with relatively low current densities, the contact area of the lattice webs 11 is widened in the electrically conductive region 12, as represented in FIG. 2. To this end, the electrically conductive layer 16 has a widening 20, which follows the profile of the lattice webs 11 and extends in the longitudinal direction of the lattice webs 11 in such a way that the region of the lattice webs 11 which comes into contact with the hollow organ is wider than the region of the lattice webs 11, in particular the carrier layer 14, further away from the hollow organ. A possible method for producing the widening 20 is disclosed in DE 10 2008 010 507, which is in the name of the Applicant and discloses the connection of the lattice webs to flexible contact elements by laser beam micro welding or adhesion or by sputtering. In the context of the invention, the method variant, according to which the widening 20 is produced by sputtering, is preferred. The content of DE 10 2008 010 507 is fully incorporated into the present application by reference.

As can furthermore be seen in FIG. 2, in addition to the widening 20, a cover 21, which is connected to the respective lattice web 11 and forms the outer surface of the respective lattice web 11, is provided. The longitudinal direction of the cover 21 in this case differs from the longitudinal direction of the respective lattice web 11 in such a way that the cover 21 extends into the adjacent cell 22 and at least partially covers the latter. In the exemplary embodiment according to FIG. 2, the longitudinal direction of the cover extends transversely with respect to the web direction. In this case, each cell is assigned a single cover 21. It is also possible for each cell to be assigned a plurality of covers 21, which are correspondingly connected to the current-carrying lattice webs. It is also possible for only a part of the cells to be provided with covers 21. In the exemplary embodiment according to FIG. 2, the cover is arranged at an angle of 90° relative to the respective lattice web, respectively in relation to the longitudinal direction of the cover 21, or of the lattice web 11. A different orientation of the cover 21 is possible. In the exemplary embodiment according to FIG. 2, the cover is formed ovally. Other geometrical shapes, for example circular covers, are possible. The same applies for the size of the cover 21, which may be adapted in such a way that the cover 21 covers the respective cell 22 with different degrees of coverage. For example, the cover 21 may cover the respective cell 22 in such a way that a narrow gap, which is sufficient to reliably prevent electrical connection, remains between the cover 21 and the lattice web 11 of the adjacent insulated region 13.

The difference between a cover 21 and a widening 20 is that the widening 20 follows the profile of the lattice web 11, i.e. it is arranged essentially parallel to the lattice web 11. The cover has a longitudinal extent which differs from the profile of the lattice web 11. Intermediate forms are possible, which combine covers 21 and widenings 20, for example widenings 20 which project laterally in relation to the associated lattice web 11, the projection extending into a cell. The covers 21 and widenings 20 form an outer layer 17 on the supporting layer 14. They may be formed from the same material as the supporting layer 14, an insulator layer 15 being arranged between the covers 21 and widenings 20, on the one hand, and the supporting layer 14, on the other hand, in the case of a conductive material.

It is also possible to form the lattice webs 11 without a widening 20. The width of the conductive layer 16 then corresponds to the width of the carrier layer 14. As represented in FIG. 1, the width of the insulation layer 15 below the cover 21 corresponds to the width of the carrier layer 14.

Figure 3:
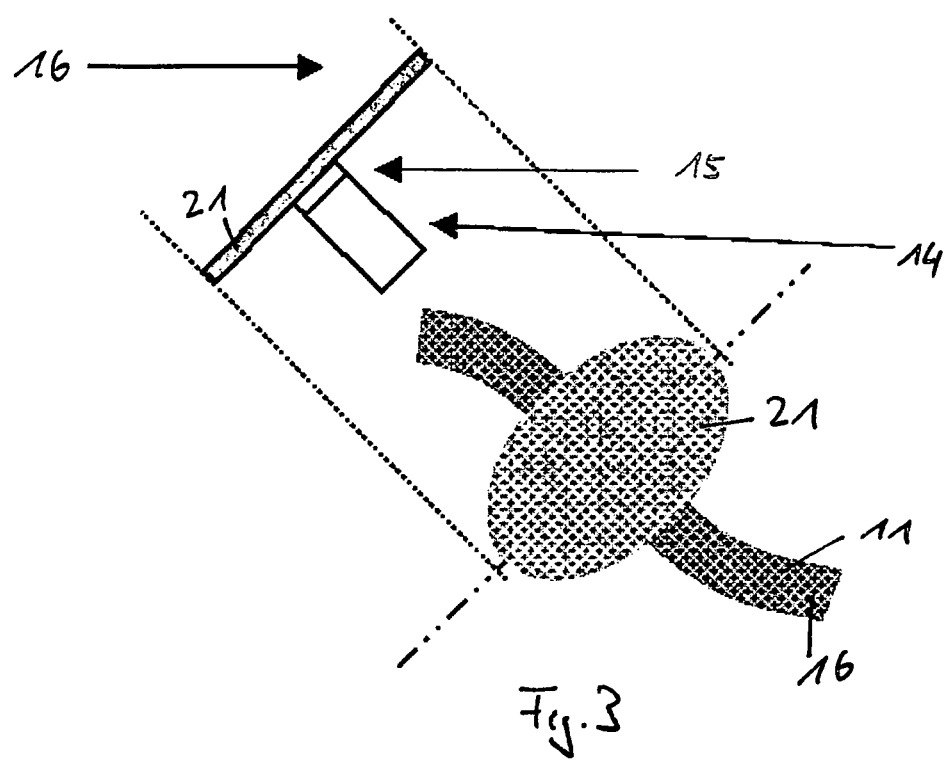
FIG. 3 shows two views of a web with a cover.
Figure 4:
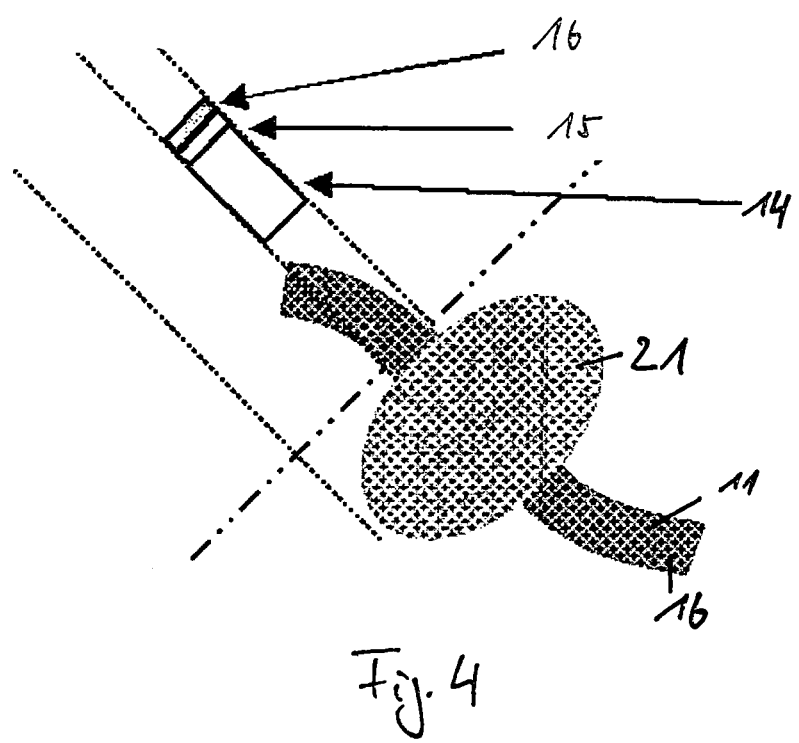
FIG. 4 shows two views of the lattice web according to FIG. 3 with a cross section which is arranged outside the cover.

As represented in FIGS. 3, 4, as well as in FIG. 2, the conductive layer 16 (with or without a widening (20)) connects the covers 21, so that the lattice webs 11 in the electrically conductive region 12 fulfill the function of the electrical supply, and furthermore function as a pole of the electrode. It is possible for the lattice webs to be formed only for the electrical supply or only as electrode poles. FIGS. 3, 4 show a plan view of a lattice web 11 with a cover 21, as well as the associated cross section through the lattice web in the region of the cover 21. The same applies for FIG. 4, the cross section through the lattice web 11 being represented in addition to the cover 21. It can be seen from FIGS. 3, 4 that the cover 21 and the electrically conductive layer 16 are arranged in the same plane of the lattice web 11. The electrically conductive layer 16 is connected to the cover 21 and is used for the electrical supply of the cover 21. Furthermore, the electrically conductive layer 16 is free in the direction of the tissue and therefore itself forms a part of the electrically active, or conductive surface of the lattice web 11.

The insulator layer 15 extends both below the electrically conductive layer and underneath the cover 21, and insulates the carrier layer 14 in the entire electrically conductive region 12. The insulator layer is likewise provided in the uncontacted, or electrically insulated regions 13. In this case, the insulator layer 16 covers the entire lattice structure. As an alternative, the insulator layer 16 may be provided only in the electrically conductive region 12, so that the carrier layer 14 forms the outer surface of the lattice structure in the electrically insulated region 13. In this case, the lattice webs 11 of the electrically conductive regions 13 are decoupled in another way from the electrical supply, for example at the piece connecting to the supply lines 23.

Figure 5:
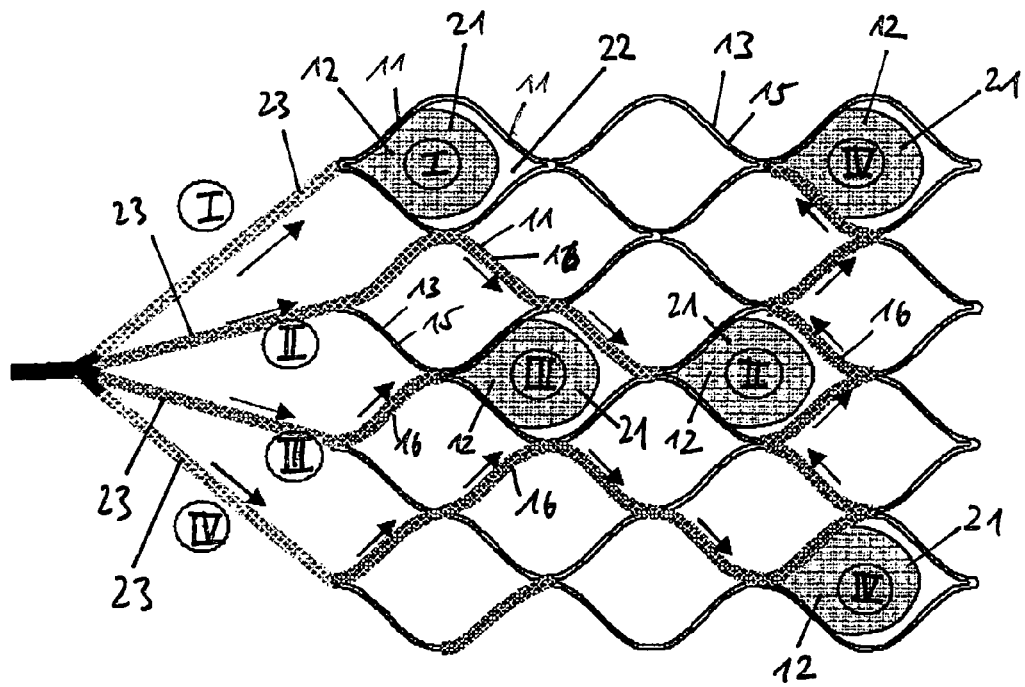
FIG. 5 shows a plan view of an electrode according to another exemplary embodiment with different electrical regions.

A method for producing the covers 21, or flap-like covers 21, represented in FIG. 5 is disclosed in DE 10 2009 060 228 and DE 10 2009 060 280, each of which is in the name of the Applicant. The content of these applications is fully incorporated into the present application by reference.

In summary, in the exemplary embodiments according to FIGS. 1 to 4 the electrically conductive layer 16, or the modulation layer, is locally interrupted, so that there are different regions 12 which are insulated from one another and are electrically conductive. Different voltages or voltage curves can therefore be applied to the electrically conductive regions 12 independently of one another. The covers 21, or web widenings 20, increase the active area for the electrical conduction and thereby reduce the current density, or with the same current strength they increase the field strengths, which leads to a gentle treatment for the surrounding tissue.

Another possibility for the arrangement of the electrode poles is shown in FIG. 5:

Specifically, the lattice structure according to FIG. 5 has four electrically insulated regions 12, which are denoted by I, II, III; IV. The four regions I-IV are connected to four different supply lines 23, which are each correspondingly denoted by I, II, III, IV. The first electrically conductive region I is formed by a single cover 21 and is located at the axial end of the lattice structure 10. The two electrically conductive regions II, III are likewise respectively formed by single covers 21, and are arranged successively in the longitudinal direction of the lattice structure. The two electrically conductive regions II, III are electrically insulated from one another, and are respectively connected to their own supply line II, III. In FIG. 5, it can be seen clearly that the electrical supply of the second electrical region II extends laterally past the third electrically conductive region III, and is separated therefrom because of the electrically insulated region 13. The second and third electrically conductive regions II, III are arranged offset with respect to the first electrically conductive region I in the circumferential direction. The fourth electrically conductive region IV is arranged behind the second electrically conductive region in the longitudinal direction, and comprises two covers 21 that are electrically connected to one another. To this end, the lattice webs 11 which are arranged in the circumferential direction, between the two covers 21 of the fourth region IV, respectively have an electrically conductive layer 16 which connects the two covers 21. Furthermore, the two covers 21 of the fourth region IV are connected to the fourth supply line IV by lattice webs 11 of the lattice structure 10 which extend in the longitudinal direction, and which likewise have an electrically conductive layer 16. The electrical supply of the fourth region IV is separated from the second region II, III, specifically by electrically insulated lattice webs 11 which can be seen in FIG. 5. The electrical feed to the respective regions I-IV is indicated by arrows. The arrangement and the number of the electrically conductive regions I-IV according to FIG. 5 is to be understood as exemplary. A different number and arrangement are possible.

The exemplary embodiment according to FIG. 5 clearly illustrates how flexibly the electrically conductive regions 12 can be distributed in the lattice structure 10. In this case, in general, it is possible to provide electrically conductive regions 12 having a plurality of covers 20, or only electrically conductive regions formed from conductive lattice webs 8, which are continuous in the circumferential direction and/or longitudinal directions, or cell-wise delimited electrically conductive regions 12 which are insulated in the circumferential direction and/or longitudinal direction from adjacent electrically conductive regions 12.

In the exemplary embodiment according to FIG. 5, the layers 16 supplying electricity extend laterally past the electrically conductive regions 12 arranged proximally, i.e. closer to the electrical supply. The electrically conductive layers 16 are in this case arranged on the same plane as the covers 21. In the multilayer system of the lattice structure 10, the electrically conductive layers 16 and the covers 21 are arranged in such a way that they belong to the same layer. The separation of the lattice webs 11 carrying current and the insulated regions 13 may, for example, be carried out by etching. This also applies for all other exemplary embodiments of this application. It is also possible to form the conductive regions 12 without covers 21 so that the webs 11, or elements which follow the webs 11, form the poles.

Figure 6:
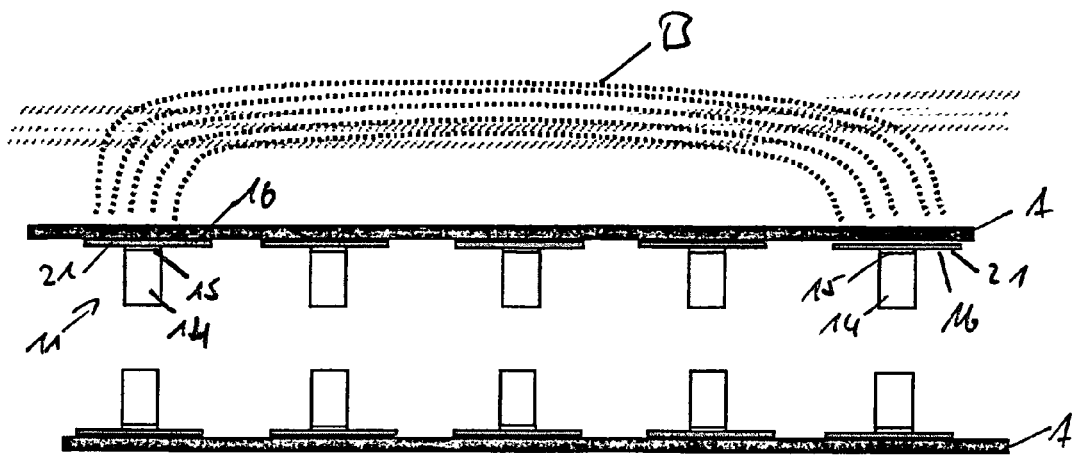
FIG. 6 shows a longitudinal section through the lattice structure of an electrode according to an exemplary embodiment according to the invention in the implanted state.
Figure 9:
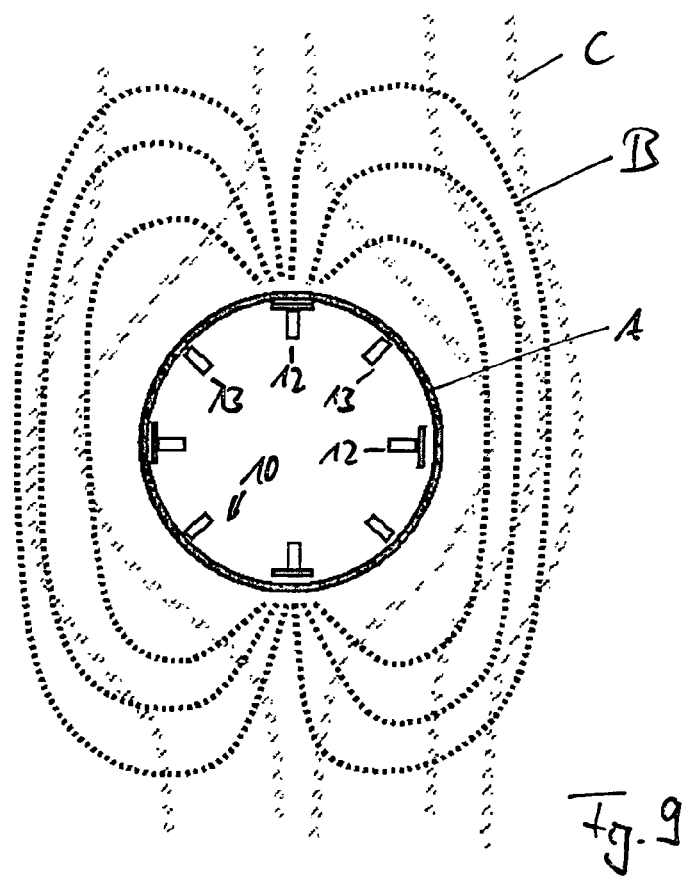
FIG. 9 shows a cross section through an electrode according to an exemplary embodiment according to the invention in the implanted state, the field lines of the electric field generated by the electrode being indicated.

Another possibility of driving, or supplying electricity to, electrically conductive regions 12 is represented with the aid of the exemplary embodiment according to FIGS. 6, 7*a*, 7*b* and FIG. 8. The structure of the electrically conductive regions 12 consists of circumferential rows, as represented in FIG. 6, which can be driven separately from one another. This is illustrated by the field lines of the electric field which are represented in FIG. 6, and which extend between the two outer rows of the electrical regions 12. As can also be seen in FIG. 7*a*, the electrically conductive regions 12 are arranged in the circumferential direction and respectively comprise a row of cells. The lattice webs 11 which form cells respectively have a conductive layer 16 as the outer surface in the conductive region 12. The conductive regions 12 form closed circumferential segments. Open circumferential segments, i.e. cell rows which do not extend over the entire circumference, are also possible. The regions 12 are separated from one another in the longitudinal direction, and respectively extend parallel to one another. The electrically conductive and electrically insulated regions 12, 13 are arranged alternately. The electrical supply of the electrically conductive regions 12 arranged successively in the longitudinal direction is carried out by line units 19, which have a plurality of electrically conductive layers 16 which are arranged above one another in the radial direction of the lattice webs, and which are respectively insulated from one another. In this case, the conductive layers 16 extend below the circumferential segments of conductive regions 12 to the circumferential segments of subsequent conductive regions 12.

The structure of the lattice webs 11 in the exemplary embodiment according to FIGS. 7*a*, 7*b* is represented in FIG. 8, which shows a lateral view of the lattice structure according to FIGS. 7*a*, 7*b*. On the carrier layer 14, an insulator layer 15 and an electrically conductive layer 16, forming a line unit 19, are arranged alternately. The outer layer forms an insulator layer 15, which respectively ends before a conductive region 12 and exposes the conductive layer 16 in this region 12. This arrangement is repeated in the successive conductive regions 12. Two electrically conductive layers 16 are arranged in the exemplary embodiment according to FIG. 8, which respectively extend between two insulator layers 15. The electrically conductive layers 16 can thus be routed underneath the electrically conductive regions 12, and respectively connect electrically conductive regions 12 arranged successively in the longitudinal direction to the electrical supply. This has the advantage that, as represented in FIG. 7*a*, continuous rows, i.e. continuous rows of electrically conductive cells or electrically conductive lattice webs in the circumferential direction, which respectively form a cell segment, can be connected to the electrical supply without interrupting the rows of electrically conductive regions 12. The conduction of the signal, or the contacting of the distally placed electrically conductive regions 12, take place along the lower layer, i.e. away from the stent surface arranged radially outward. This design is simple and makes it possible to subdivide the electrode into a large number of electrically conductive circumferential segments which are independent of one another. The number of electrically conductive layers for supplying different electrically conductive regions 12 may be extended in any desired way. A line unit 19 having at least two electrically conductive layers, in particular having 3, 4, 5, 6, 7, 8 or more electrically conductive layers, is therefore disclosed.

In summary, there are various possibilities for the arrangement of the electrode poles:

In the exemplary embodiment according to FIG. 2, the electrically conductive regions 12 are arranged in the longitudinal direction of the lattice structure 10 and are electrically insulated from one another in the circumferential direction. As represented in the exemplary embodiment according to FIG. 5, the electrically conductive regions 12 may additionally be arranged in the circumferential direction and electrically insulated from one another in the longitudinal direction. Arrangement of the electrically conductive regions 12 only in the circumferential direction and insulation thereof in the longitudinal direction is shown in FIG. 7*a*.

Figure 10:
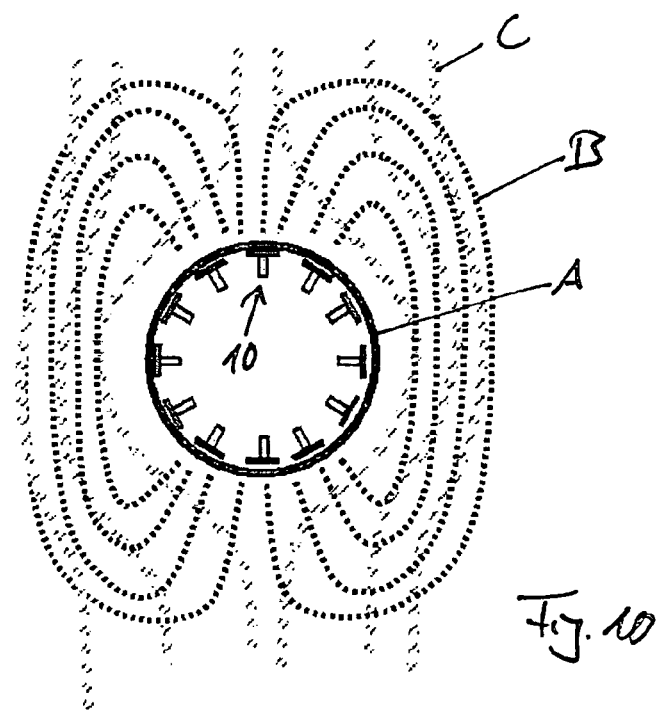
FIG. 10 shows a cross section through an electrode according to another exemplary embodiment according to the invention with an increased number of lattice webs.

The functionality of the electrode according to the exemplary embodiments described above will be explained in more detail with the aid of FIGS. 9 to 13, which in principle correspond to the structure of the electrode according to FIG. 2 and in which an electric field is generated between two opposite electrically conductive regions 12. The good modulation capacity of the electrode is revealed, for example, by FIG. 9. The resulting electric field is denoted by field lines, which predominantly extend parallel to the plane which extends through the two electrical regions 12 to which voltage is applied. By increasing the number of poles of the electrode, or of the electrically conductive region, as represented in FIG. 10, the modulation can be finely adjusted. It is furthermore possible to adapt the modulation to the physiological response. By modifying the modulation regions, the distance and/or the direction of the nerves to be stimulated can be modified, without the position of the electrode having to be changed.

Figure 11:
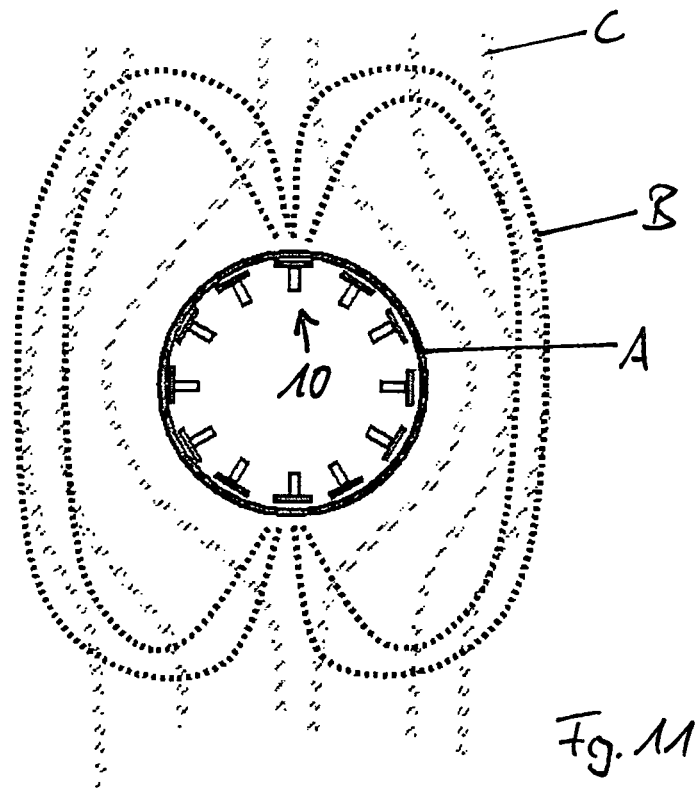
FIG. 11 shows the electrode according to FIG. 10 with a modulated electric field.
Figure 12:
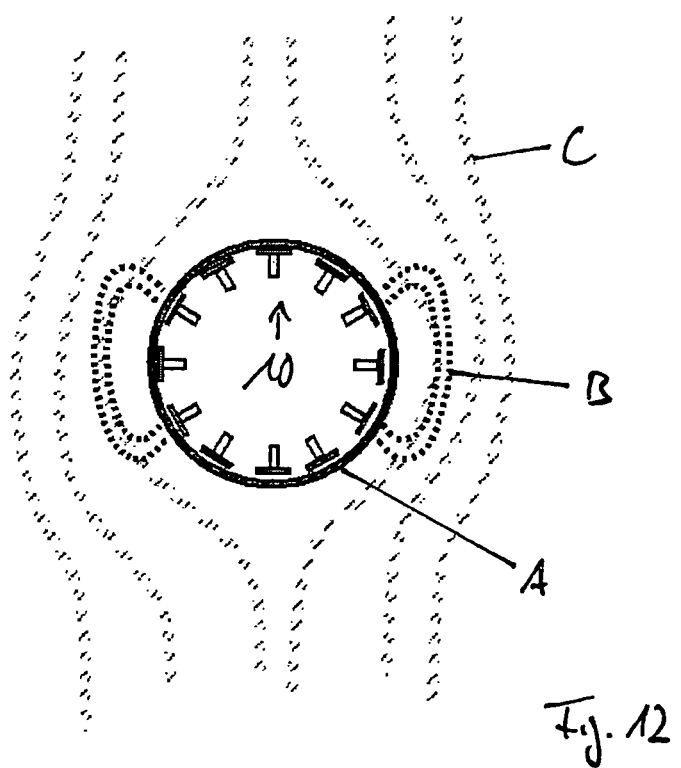
FIG. 12 shows the electrode according to FIG. 10 with another modulated field.
Figure 13:
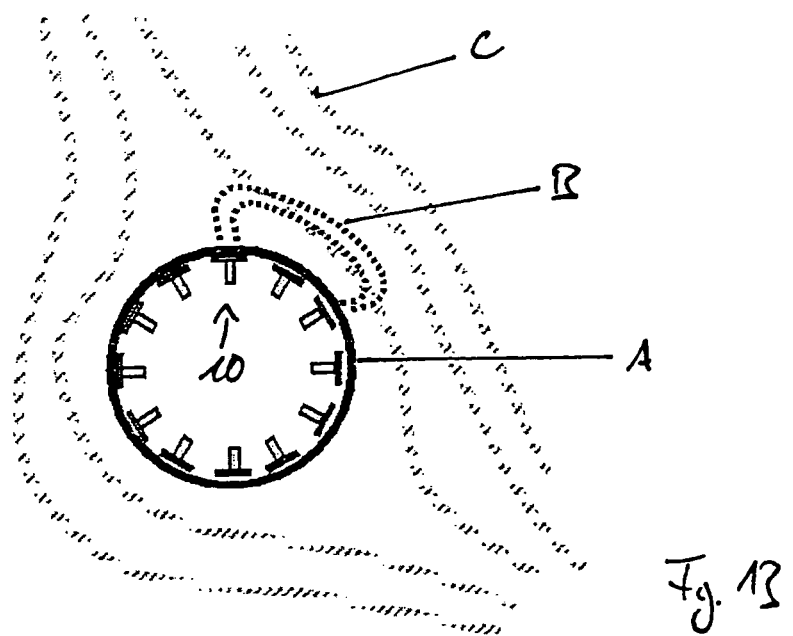
FIG. 13 shows the electrode according to FIG. 10 with another modulated electrical field.

Furthermore, the intensity of the modulation can be modified without substantially varying the voltage and therefore the current density. In the mode of operation according to FIG. 10, a large number of nerves is achieved by activating a plurality of poles, or electrically conductive regions 12. In this case, nerves in proximity to the electrode and remote from the electrode are stimulated. The direction of the electric field is adjusted by the selection of the electrical regions, and in the exemplary embodiment according to FIG. 10 extends from the top downward. In the mode of operation according to FIG. 11, only the nerves remote from the electrode, which are arranged further distally from the hollow organ, are stimulated. The nerves in proximity to the electrode, enclosing the hollow organ, are not stimulated. To this end, as represented in FIG. 11, voltage is applied only to the two diametrically opposite poles, or electrically conductive regions 12. In the mode of operation according to FIG. 12, only the laterally extending nerves in proximity to the electrode are stimulated. To this end, the electrically conductive regions 12 which are arranged in the vicinity of the nerves to be stimulated are driven. As can be seen in FIG. 13, in the case of a different nerve arrangement, the position of the modulation regions can be modified straightforwardly without the position of the electrode having to be changed.

The modulation may be adapted to the response of the body, or of the organ. In the case of nerve modulation to suppress pain, the response may be given directly by the patient's sensation. This also applies for diseases with obvious symptoms, such as Parkinson's or epilepsy. In this case, the parameters of the electrode may be adjusted actively by the doctor. In the case of other conditions, such as depression, but also for the diseases as described above, hormonal studies may be carried out which may then lead to readjustment of the modulation parameters. Increasing the stimulation of circulation is possible, for example, by measuring the blood flow using Doppler methods. In these cases, the modification of the modulation parameters of the electrode is formed by the doctor. By the modulation, it is possible to treat circulatory problems, such as flow problems or blood pressure problems. In particular, the endovascular neuromodulation may be used to treat vascular diseases such as hemorrhagic and ischemic stroke by influencing circulatory parameters such as blood pressure and blood flow, in particular by vascular widening. It is also possible for the electrode to have regions which are adapted for signal acquisition. In these regions, currents are induced by the nerve activity and are processed, or amplified, to form corresponding signals. A configurational modification of the modulation regions may in this way be carried out automatically by the system. The means required for the signal acquisition are known per se and can readily be combined with the electrode.

In the operating modes according to FIGS. 9 to 13, the poles of the electric field, or of the electrode, are formed by the different electrically conductive regions 12 of the lattice structure 10. It is also possible for one electrically conductive region 12, several or all the electrically conductive regions 12 to have the same voltage applied to them, and for a further electrode to be provided for generating the electric field. The further electrode may, for example, be arranged extracorporeally. The second electrode may also be a wire, is connected to the system, or the tip of a catheter which is used for introducing the electrode into the body.

The electrode is produced by a method in which the lattice structure 10 is produced at least partially by physical vapor deposition. With this method, it is possible to deposit various materials, in particular electrically insulating materials and electrically conductive materials, layer-wise on a substrate, in order to form the electrically insulated and electrically conductive regions 12, 13 described in connection with the various exemplary embodiments. In this case, the structures produced by the PVD method may be structured further by etching methods known per se, so that the structures described in the exemplary embodiments are obtained. It is possible to produce self-supporting lattice structures which are formed fully by the layer-wise vapor deposition of materials. As an alternative, a conventionally produced web structure, for example a web structure produced by laser cutting, may be coated with various materials by a PVD method, in order to form the layer-wise constructed lattice webs represented in the exemplary embodiments. By the use of suitable materials, the electrically conductive regions 12 and the electrically insulated regions 13 can be produced straightforwardly. Possible production methods are disclosed in DE 102006007231 and DE 102005018731, the content of which is respectively incorporated fully into the present application by reference.

LIST OF REFERENCES 10 lattice structure
11 lattice webs
12 electrically conductive region
13 electrically insulated region
14 carrier layer
15 insulator layer
16 electrically conductive layer
17 outer layer
18 inner layer
19 line unit
20 widening
21 cover
22 cells
23 supply lines
24 central supply

The invention claimed is:

1. An electrode for medical applications for neuromodulation and/or nerve stimulation and/or neurological signal acquisition, which is compressible and expandable for introduction into a hollow organ of a body and is coupled or couplable to an electrical supply, wherein the electrode is characterized by a compressible and expandable lattice structure comprising lattice webs which form cells, the lattice structure being coupled or couplable to the electrical supply and forming a plurality of electrically conductive regions and a plurality of electrically insulated regions, wherein the electrically conductive regions and the electrically insulated regions are arranged at different positions along the lattice structure, the electrically conductive regions being separated from one another by the electrically insulated regions with all of the electrically conductive regions being insulated from one another, wherein different electrically conductive regions can be variably interconnected with one another for the modulation of electric fields, wherein the different electrically conductive regions are coupled or couplable to the electrical supply by electrically conductive layers along different lattice webs electrically insulated from one another and/or by a plurality of line units in at least one lattice web.

2. The electrode as claimed in claim 1, wherein at least one section of the lattice structure or the entire lattice structure is constructed in layered fashion.

3. The electrode as claimed in claim 1, wherein the plurality of electrically conductive regions are arranged in an outer surface and/or in an inner surface of the lattice structure.

4. The electrode as claimed in claim 1, wherein the lattice structure has a carrier layer, at least one insulator layer and at least one electrically conductive layer.

5. The electrode as claimed in claim 4, wherein in the plurality of electrically conductive regions, the insulator layer is arranged between the carrier layer and the electrically conductive layer.

6. The electrode as claimed in claim 4, wherein in the plurality of electrically insulated regions, the insulator layer forms the outer layer of the lattice structure.

7. The electrode as claimed in claim 1, wherein the lattice structure has at least one line unit comprising at least two insulator layers, an electrically conductive layer being arranged between a first and a second insulator layer.

8. The electrode as claimed in claim 7, wherein the first insulator layer forms the outer layer in the plurality of electrically insulated regions, a further electrically conductive layer, which forms the outer layer in the plurality of electrically conductive regions, being arranged on the first insulator layer in the plurality of electrically conductive regions.

9. The electrode as claimed in claim 7, wherein the lattice webs have, in the plurality of electrically conductive regions, an electrically conductive widening which extends in the longitudinal direction of the lattice webs in such a way that the widening is wider than the carrier layer.

10. The electrode as claimed in claim 1, further comprising at least one electrically conductive cover, wherein at least one lattice web is connected to the at least one electrically conductive cover, a longitudinal direction of which differs from a longitudinal direction of the lattice web in such a way that the cover extends into at least one adjacent cell and at least partially covers the latter.

11. The electrode as claimed in claim 10, wherein the size and/or geometry of the at least one cover is at least partially equal or different and/or the number of covers varies on the circumference of the lattice structure and/or in the longitudinal direction.

12. The electrode as claimed in claim 10, wherein the at least one cover comprises a plurality of covers connected to one another by an electrically conductive layer or a line unit.

13. The electrode as claimed in claim 1, wherein the electrically conductive regions are adapted for the generation of electric fields and/or for signal acquisition on the basis of nerve activities.

14. The electrode as claimed in claim 1, wherein the plurality of electrically conductive regions are arranged mutually parallel at least in sections along the lattice structure and/or are arranged in series at least in sections along the lattice structure and are separated by electrically insulated regions.

15. The electrode as claimed in claim 1, wherein the plurality of electrically conductive regions are arranged laterally next to one another as seen in the cross section of the lattice structure and are separated by electrically insulated regions.

16. A system having an electrode as claimed in claim 1, an electrical supply, a pulse generator and control electronics, which are coupled or couplable to the electrode.

17. The system as claimed in claim 16 wherein at least one further electrode for medical applications is provided.

18. A method for producing an electrode as claimed in claim 1, wherein the lattice structure is produced at least partially by physical vapor deposition, various materials being deposited layer-wise on a substrate and structured in such a way that a self-supporting lattice structure or a coated lattice-like carrier structure comprising at least one electrically conductive region and at least one electrically insulated region is formed.

* * * * *